United States Patent [19]

Rhodes et al.

[11] Patent Number: 5,843,482
[45] Date of Patent: Dec. 1, 1998

[54] PRODUCTS AND PROCESSES FOR THE TREATMENT OF THE ALIMENTARY CANAL

[75] Inventors: John Rhodes, Cardiff; Brian Kenneth Evans, Dinas Powys, both of Wales

[73] Assignee: Tillotts Pharma AG, Ziefen, Switzerland

[21] Appl. No.: 966,163

[22] PCT Filed: Jul. 19, 1991

[86] PCT No.: PCT/GB91/01209

§ 371 Date: Jan. 21, 1993

§ 102(e) Date: Jan. 21, 1993

[87] PCT Pub. No.: WO92/01457

PCT Pub. Date: Feb. 6, 1992

[30] Foreign Application Priority Data

Jul. 20, 1990 [GB] United Kingdom .................. 9015988
Jan. 25, 1991 [GB] United Kingdom .................. 9101675
Feb. 22, 1991 [GB] United Kingdom .................. 9103795

[51] Int. Cl.$^6$ .......................... A61K 33/24; A61K 31/65; A61K 31/415
[52] U.S. Cl. ......................... 424/653; 514/152; 514/394; 514/395; 514/925; 514/926
[58] Field of Search .................... 424/653; 514/925, 514/926, 152, 394, 395

[56] References Cited

U.S. PATENT DOCUMENTS

| 3,887,448 | 6/1975 | Schulze | 204/130 |
| 4,837,378 | 6/1989 | Borgman | 424/81 |
| 4,940,695 | 7/1990 | Coveney et al. | 514/57 |
| 5,008,256 | 4/1991 | Clitherow | 514/184 |
| 5,128,140 | 7/1992 | Chapura et al. | 424/451 |
| 5,196,205 | 3/1993 | Borody | 424/653 |

FOREIGN PATENT DOCUMENTS

| 0 217 440 | 4/1987 | European Pat. Off. . |
| 0 282 132 | 9/1988 | European Pat. Off. . |
| 0 367 484 | 5/1990 | European Pat. Off. . |
| 25 01 787 | 7/1975 | Germany . |
| 2 220 855 | 1/1990 | United Kingdom . |

OTHER PUBLICATIONS

Hutton et al., "Mucolysis Of The Colonic Mucus Barrier By Faecal Proteinases: Inhibition By Interacting Polyacrylate", Clinical Science, 1990, vol. 78, pp. 265–271.
"Methylcellulose And Stabilising And Suspending Agents—5409–w Carbomer", p. 950, Martindale, 28th Edition, 1982.
Derwent Abstract 10879 B/06—JP–A–53148538, entitled "Anti–anaemia Compositions For Warm–Blooded Animals—Contains Iron Salts And Sodium Polyacrylate".

*Primary Examiner*—Kevin E. Weddington
*Attorney, Agent, or Firm*—Foley & Lardner

[57] ABSTRACT

Complexes of bismuth, e.g. bismuth salts, and polyacrylate, e.g. carbomer, are discloses which may be incorporated into pharmaceutical compositions for oral, oral delayed-release, and rectal administration. The complexes may be combined with an antibiotic, such as tetracycline, and an antiprotozoal agent, e.g. Metronidazole, for use in the treatment of *Helicobacter pylori* infection. The treatment of inflammatory bowel disease using bismuth/polyacrylate complexes, or other bismuth preparations, is also described.

21 Claims, No Drawings

PRODUCTS AND PROCESSES FOR THE TREATMENT OF THE ALIMENTARY CANAL

This invention relates to products and processes for the treatment of the alimentary canal, the use of bismuth and novel complexes thereof for treating conditions of the alimentary canal.

Bismuth compounds have been used medically for over 150 years, originally being used in the treatment of treponeme infection, e.g. syphilis, and latterly as dusting powders, antacids, astringents and in the treatment/prophylaxis of traveller's diarrhoea. More recently, bismuth salts have been used in the treatment of gastric and duodenal ulcers. However, it is likely that such salts are precipitated in the low pH environment of the stomach and thereby will be less likely to be biologically active further along the gut. It has also been known to use suppositories and ointments containing bismuth to treat haemorrhoids.

There has been a need to improve the pharmacological effectiveness of bismuth while minimising its absorption from the gut. The desired action of bismuth is local, and absorption leads to unwanted side-effects which may limit the duration, dosage or intensity of treatment.

We have discovered that bismuth forms a water soluble complex with polyacrylates and that the soluble complexes are particularly useful in treatment of conditions of the alimentary canal. Moreover, they have the advantage of being very poorly absorbed from the gut.

One aspect of our invention provides a water soluble complex of bismuth with a polyacrylate.

We surmise that bismuth complexes with the anionic carboxyl groups of the polyacrylate and does not readily precipitate at acid pH, although our invention is founded on empirical evidence and not on any theory of action.

Preferably, the polyacrylate is a carbomer, such as those described in the British Pharmacopoeia and defined in CAS 54182-57-9, which generally consists of a polymer of acrylic acid cross-linked with allylsucrose, and contains 56 to 68% carboxylic acid groups. Preferred carbomers are carbopol 934P and 974P (available from Goodrich UK).

Until recently, carbomer has been used in the pharmaceutical and cosmetic fields as stabilisers, binding agents, emulsifiers and gel-forming excipients. In GB 2,220,855 (Reckitt & Coleman) polyacrylates of the carbomer type are suggested for use alone in the treatment of inflammatory bowel disease.

It is noted that carbomer has been reacted with basic drugs, such as ephedrine, but it has not been suggested previously that polyacrylates might form a soluble complex with heavy metal ions like bismuth and thereby modify their pharmacological effect and metabolic fate.

We prefer to use a bismuth salt to prepare the complex and prefer salts with weak inorganic acids or organic carboxylic acids, e.g. selected from bismuth citrate, bismuth carbonate, bismuth subsalicylate and bismuth subgallate. Bismuth hydroxide may also be used. Other salts, such as bismuth subnitrate, and bismuthates, such as tripotassium dicitrato bismuthate, may be used. The complex preferably comprises carbopol 934P and bismuth derived from bismuth citrate.

It is also possible to use bismuth combined with ligands, such as coordinating ligands, and ligands or cations from the salts mentioned above may become incorporated into the complex. It is clear therefore that the cation or ligand used must be carefully selected since it may be released from the complex in use.

The complex may be prepared by reacting a suitable bismuth compound, e.g. a salt with a weak acid, preferably with an aliphatic or aromatic carboxylic acid, with a dispersion of the carbomer. If desired an acid acceptor may be present or preferably may be added subsequently to combine with the acid liberated from said salt and produce a final pH e.g. in the range 5 to 8. For example, bismuth citrate and bismuth subsalicylate may be used as said bismuth compound; in the case of bismuth citrate, it is desirable to add sodium hydroxide or other acid acceptor at the end of the reaction to increase the water solubility of the carbomer-bismuth complex, neutralise the citric acid liberated and maintain the pH necessary to give the desired viscosity in the carbomer solution.

The reaction may take several days e.g. 2 to 12 days standing at room temperature, but can be accelerated by constant stirring and heating, e.g. to 40° C. or higher. A temperature of 40° C. with stirring overnight will usually produce the complex within 24 hours. Aqueous reaction media will often be used, but non-aqueous or aqueous/organic media can also be used if the solubilities of the reactants are appropriately selected. Another alternative is to incorporate the bismuth in the carbomer during its preparation.

The ratio of bismuth to carbomer for the formation of soluble complexes can be varied, there being sufficient carbomer to solubilise the bismuth but preferably not so much that over-viscous solutions are produced. A stoichiometric ratio of carboxyl groups to bismuth ions tend to result in an unduly low viscosity of solutions containing the complex. Therefore an excess of carbomer is preferred. The weight ratio of reactants used of course depends on the bismuth compound used and on the proportion of free carboxyl groups in the carbomer. For example, using Carbopol 934P and bismuth citrate, the ratio may be in the range 7:1 to 1:5, preferably about 2:1 by weight. If the ratio of bismuth to carbomer is too great then the carbomer becomes supersaturated. The complex so formed very readily releases bismuth in the intestine as it reaches equilibrium with intestinal fluid.

The soluble complex may be extracted by conventional techniques such as, by precipitation from an aqueous medium with a water-miscible organic solvent e.g. methanol.

We have found that the complex according to the invention is particularly effective in the treatment of conditions of the alimentary canal although other conditions may be beneficially treated using a pharmaceutical composition comprising a complex according to the invention.

The complex may be incorporated into a pharmaceutical composition to be administered either rectally, e.g. as an enema, or orally, for example, in coated tablets or capsules as described below. Also, the complex may be formed into microgranules and coated, for example with Eudragit-L or S and contained within a capsule similarly coated. In all solid compositions it is preferable to include a disintegrant. Still further, bismuth/polyacrylate complexes may be formulated in a number of dosage forms, e.g. uncoated or coated solid dosage forms for non-delayed release or delayed release oral administration.

Upper alimentary conditions of interest, include for example, peptic ulcer of the oesophagus, stomach or duodenum and mucosal inflammation (oesophagitis, gastritis and duodenitis). In general, mucosal inflammation of the alimentary tract is often related to pernicious infection with *Helicobacter pylori* (previously classified as *Campylobacter pylori*) and such infection may be successfully treated with bismuth preparations. Heretofore a popular treatment of *Helicobacter pylori* infection has required four daily doses of bismuth tablets, tetracyline tablets and metronidazole tablet (metronidazole being a preferred anti-protozoal drug) whereas pharmaceutical compositions comprising the bismuth/polyacrylate complex according to the invention may be formulated or complexed with tetracyline and metronidazole (2-methyl-5-nitroimidazole-1-ethanol) for only twice daily administration. The invention also includes therefore pharmaceutical compositions comprising the bismuth complex and one or more further pharmacologically active compounds e.g. antibiotics or anti-protozoal agents.

Some small intestinal and colonic conditions are associated with identifiable infective organisms. Two organisms of note are Cryptococcus and Microsporidium. These organisms sometimes occur in water supplies and cause severe diarrhoea, especially in patients with AIDS. Pharmaceutical compositions according to the invention, preferably in post-gastric delayed release dosage form may be administered orally to patients to combat infections such as these. Other such formulations may be prepared to take advantage of the benefits of a bismuth/polyacrylate complex according to the invention.

It is a notable aspect of our invention that a bismuth/polyacrylate complex is also particularly useful in the treatment of inflammatory bowel disease such as ulcerative colitis and Crohn's disease involving the colon.

Numerous compounds have been examined in the last twenty years to find effective measures for the treatment of inflammatory bowel disease. Such compounds include arsenicals, disodium cromoglycate, flagyl, lignocaine, 4- and 5-aminosalicylic acid as rectal preparations and orally administered thalidomide and cyclosporin. Rectal arsenic has been shown to be highly effective in ulcerative proctitis but is no longer widely used and, indeed, the therapeutic use of inorganic arsenical preparations is no longer recommended. The wide diversity of treatments is an indication of the complexity and intransigence of this condition.

So far the only effective forms of medical therapy for ulcerative colitis are corticosteroids and aminosalicylates but approximately one third of patients fail to go into complete remission despite conventional therapy.

In spite of many attempts to provide an effective treatment for inflammatory bowel disease, this chronic, distressing and ultimately life-threatening condition has not been well controlled.

Although bismuth/polyacrylate complexes appear to have distinct advantages in the treatment of inflammatory bowel disease, we have found that other compounds of bismuth may also be used for this purpose. The bismuth compound should be rectally administered, or post-gastrically available, and is preferably used in combination with a stabilising agent, to provide a novel and effective treatment of inflammatory bowel disease.

Thus a further aspect of our invention provides the use of a compound containing bismuth in the preparation of a rectally administered pharmaceutical composition or delayed-release oral composition for the treatment of inflammatory bowel disease.

Another aspect of our invention provides a pharmaceutical composition for rectal administration for the treatment of inflammatory bowel disease characterized in that it comprises a compound containing bismuth and a thickening/gelling agent.

The composition may be in a form suitable for use as a fluid or foam enema, or as a concentrate for use in the preparation of an enema or in the form of a suppository.

While it is preferred to use a bismuth/polyacrylate complex, other salts, especially with weak or organic acids, may be used, e.g. bismuth citrate, bismuth carbonate, bismuth subsalicylate, bismuth subgallate, or less preferably bismuth subnitrate may be used. Also, bismuthates such as tripotassium dicitrato bismuthate may be used.

The thickening/gelling agent may be selected from any which are pharmaceutically acceptable and thicken or form gels with aqueous media. Preferably the agent is selected from polyacrylates, e.g. carbomers, such as Carbopol 934P, although cellulose derivatives, especially hydroxyalkyl ethers such as hydroxypropyl, hydroxyethylmethyl, and hydroxyethyl cellulose, and gums of microbial or vegetable origin, e.g. xanthan gums, for example Keltrol may be used. Of course it will be apparent to a skilled person that the thickening/gelling agent may be selected so that it only exhibits the required thickening/gelling properties in the conditions of the colon and rectum. In this respect it should be noted that the viscosity of carbomer-containing aqueous compositions may be varied by changes in pH and/or ionic strength. Thus a pharmaceutical composition according to the invention may be formulated for ease of administration yet exhibit the desired thickening/gelling qualities once administered.

Dosage rate will depend on mode of application, dosages per day, size of patient etc. and will be readily determined by the skilled person. A preferred formulation for an enema would comprise, for example, a bismuth compound, e.g. bismuth citrate, in a unit dosage in the range 300 mg to 1,600 mg, preferably 400 mg to 800 mg, suspended in an aqueous carrier, preferably of about 100 ml; the formulation preferably contains 0.1 to 2.0% carbomer, e.g. Carbopol 934P, more preferably 0.4 to 1.0% and desirably the bismuth and carbopol are present as a complex.

Depending on the nature of the thickening/gelling agent, it may be preferable to use an antioxidant and/or preservative such as a metabisulphite or methyl/propyl hydroxybenzoate. The amount of such an agent will be apparent to a skilled person and, again, is dependent on the form of administration.

Enema foams will comprise suitable foam bases containing expanding agents, surfactants and foam-stabilisers.

It is a surprising and valuable feature of our invention that absorption of bismuth, as measured by bismuth serum levels, is minimal even after prolonged administration.

It is also possible to provide a composition which is not administered rectally but per os and only becomes available to the patient after passing through the stomach.

A further aspect of our invention provides a delayed or substained-release pharmaceutical composition for oral administration characterized in that it comprises a compound containing bismuth which is released post-gastrically.

In order to achieve the desired delayed or sustained-release, it is preferable to form the composition as a tablet or capsule, e.g. a gelatin capsule, having a coating of acidic material substantially insoluble in the gastric fluid and of limited solubility in alkaline media.

A sustained-release formulation can be achieved by either using a microgranular formulation of the bismuth compound coated with a semi-permeable membrane such as ethylcellulose or by coating the granules with a lacquer consisting of an acrylic resin based on acrylic and methacrylic acid esters containing a low content of quaternary ammonium groups at a predetermined molar ratio. suitable resins include EUDRAGIT RL and RS. The coated granules may then be compressed into tablets or packed into hard gelatin capsules suitable for oral administration.

As acidic material for the coating of oral compositions of the invention for delayed-release anionic polymers, particularly anionic acrylate polymers and especially anionic polymers synthesised from methacrylic acid and methyl methacrylate, may be used. Carboxyl groups in such polymers render the material capable of forming salts in alkaline environments in which they are sparingly soluble while in the acid to neutral pH range the coatings will be substantially insoluble and substantially impermeable thus protecting the active ingredient contained within from gastric acids.

The coatings may be applied conventionally, typically as a lacquer or solution containing the acidic material from which the solvent or carrier is then evaporated.

A particularly suitable acidic material for coating the compositions of the invention for lower bowel treatment is the anionic methacrylate polymer sold under the registered Trade Mark EUDRAGIT S by Röhm Pharma GmbH of Darmstadt, West Germany. Earlier investigations revealed that capsules coated with EUDRAGIT S100 disintegrate in the ascending colon of the patients to whom the capsules were administered. In general EUDRAGIT S has previously been recommended only for mixture with more soluble polymers in order to retard release, and has not been envisaged as the sole coating material. EUDRAGIT S is a copolymer of methacrylic acid and methyl methacrylate in which the ratio of free carboxyl groups to ester groups is approximately 1:2 and having a mean molecular weight of 135,000. Coatings of acidic materials, such as that sold as EUDRAGIT L (composition as EUDRAGIT S but having a carboxyl/ester ratio of 1:1), may be used in the coating of tablets or capsules to release active agents in the small intestine, although they may be applied in much greater thicknesses than was hitherto conventional thereby delaying release of the active agent until the tablet or capsule reaches the large intestine. It will be apparent to the skilled person that mixtures of substances, such as EUDRAGIT S and EUDRAGIT L, may be used as coating materials.

In general coating thicknesses of about 25 to 200 $\mu$m, and especially 75 to 150 $\mu$m, are preferred using about 3 to 25 mg, preferably 8 to 15 mg of acidic coating material per $cm^2$ of tablet or capsule surface. The precise coating thickness will however depend upon the solubility characteristics of the acidic material used and site to be treated.

Together with the acidic material, the coating material may contain additives such as coloring agents, plasticisers, opaque film coatings, gloss producers and auxiliary materials (e.g. talc).

As referred to above, the provision of the coating to the compositions of the invention may be achieved in conventional manner, e.g. by the use of spraying, fluidized bed, immersion tube and immersion blade techniques. (See for example D. Dreher "Film coatings on acrylic resin basis for dosage forms with controlled drug release" Pharma International ½ (1975) 3 ).

In microgranular formulations, suitably the granules are 0.25 to 4 mm, usually 0.25 to 2.5 mm, especially 0.4 to 1.5 mm and particularly about 0.6 mm, diameter.

The coating can be applied to the granules by any suitable known coating technique. In particular, conventional coating techniques such as spray or pan coating can be employed. (See for example D. Dreher, supra). Preferably, the coating is applied from aqueous suspension.

The granular coating material can be any suitable coating, e.g. cellulose acetate phthalate, hydroxypropyl methyl cellulose phthalate, ethyl cellulose or polyvinyl acetate phthalate but the preferred coating material is an anionic polymer, especially one having the dissolution profile specified in EP-A-0097651. The presently preferred polymers are anionic carboxylic polymers, e.g. EUDRAGIT L or S described above.

The thickness of coating required on the granules will depend upon the dissolution profile of the particular coating materials and possibly also upon the dissolution profile of the enteric coating on the capsule. However, it is well within the ability of the man of average skill in the art to determine by trial-and-error experimentation the optimum thickness of a particular coating required for a particular dosage form of the invention. When using an aqueous dispersion of a partly methyl esterified methacrylic acid polymer of the EUDRAGIT S type, the amount of coating material usually will be between 20 and 25% (dry weight basis) with 21 to 23% being preferred.

The coating can, and usually will, contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate, although the presence of such a plasticiser may not be necessary when using an aqueous suspension for coating.

Usually, the capsule into which the coated granules are loaded will be a soft or, preferably, hard gelatin capsule although other capsules which will dissolve in the small intestine can be used. The capsule is coated with an enteric coating which will protect it during passage through the stomach. Any conventional enteric coating material which is soluble in the small intestine can be used, e.g. cellulose acetate phthalate, hydroxy propylmethyl cellulose phthalate or initially ethyl cellulose followed by polyvinyl acetate phthalate, but it is preferred to use an anionic polymer having an appropriate dissolution profile. The presently preferred polymers are anionic carboxylic polymers, e.g. EUDRAGRIT L.

The enteric coating can, and usually will contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate.

Conventional coating techniques such as spray or pan coating are employed to apply the enteric coating (see for example D. Dreher, supra).

In addition to the active bismuth containing compound the tablet or capsule cores for the compositions of the present invention may also contain additives such as fillers (e.g. lactose or dicalcium phosphate), binders (e.g.starch or polyvinylpyrrolidone), lubricants (e.g. magnesium stearate, stearic acid or talc) and disintegrants (e.g. alginic acid or sodium starch glycolate). The tablet or capsule cores may be prepared in a conventional manner. For some delayed release applications it will be preferable to combine the bismuth complex in a matrix of hydrophobic paste.

It is preferable to include a suitable disintegrant, such as Explotab (a brand of sodium starch glycollate made by K&K Greef), or Primojel (from AVEBE, Netherlands) in the orally administered compositions according to the invention.

The invention will now be illustrated by the following non-limiting Examples.

EXAMPLE 1

900 mg of carbomer (Carbopol 934P; B. F. Goodrich) is evenly dispersed by vigorous stirring in 100 ml of water and then 450 mg of bismuth citrate (BPC 1949) is added with stirring. The stirring is continued throughout but not vigorously and a sodium hydroxide solution of known strength, preferably 20% w/v, is gradually added until a viscous solution (gel) is formed and the pH is adjusted to between 6 and 7.5, although a wider pH may be used (e.g. from 5 to 8). Gentle stirring is then continued until the reaction is complete at which time the carbomer/bismuth complex may be extracted from the aqueous solution by precipitation with methanol. After extraction, it may be dried and subsequently used either in dry formulations or re-solubilised for use in an enema.

EXAMPLE 2

Bulk preparation of bismuth citrate enemas containing the following ingredients:

| | |
|---|---|
| Bismuth Citrate | 225 g |
| Carbomer 934P | 450 g |
| Keltrol | 100 g |
| Lecithin | 100 ml |
| Methylhydroxybenzoate | 75 g |
| Propyl hydroxybenzoate | 7.5 g |
| Sodium Hydroxide 20% w/v | 500 ml* |
| Filtered Water | to 50 l. |

The carbomer and Keltrol were added gradually to rapidly stirred volumes of cold water and stirring was continued until a viscous suspension and solution respectively were formed. Methyl and propyl hydroxybenzoate, previously dissolved in boiling water, were added to the viscous Keltrol solution. Bismuth citrate was mixed with lecithin and added slowly to the Keltrol solution with constant stirring. The carbomer solution was then added slowly with stirring; once the mixing was complete approximately 500 ml of sodium hydroxide solution was added to bring the pH into the range 6.8–7.4 (optimal 7.0). The resulting thixotropic preparation was distributed in 100 ml enema bags in 100 ml aliquots.

EXAMPLE 3

Bismuth citrate (225 g) was dispersed in the carbomer suspension as prepared in Example 2. The required amount of sodium hydroxide solution (20% w/v) was the added to bring the pH to about 7.0. After stirring overnight, the resulting gel was mixed with an equal volume of methanol which caused precipitation of the carbomer-bismuth citrate complex. The preparation was centrifuged and the supernatant discarded. The remaining slurry was freeze dried to produce a dry powder for later use. This dry powder, on mixture with water, readily reconstitutes a viscous gel which is clear and pharmaceutically acceptable.

EXAMPLE 4

Samples were made with bismuth citrate (430 mg)+ carbomer (900 mg)+$H_2O$ (100 ml)+NaOH pellets (410 mg). Following vigorous stirring this was left overnight to go translucent indicating that the reaction had taken place. The gels were precipitated with methanol (150 ml to 200 ml). The white precipitate was pelleted by centrifugation (1500 rpm, 30 min), the supernatant decanted, and the precipitate freeze dried. The dried precipitate was powdered before despatch. The content of Bi was 15.2 wt %.

Further samples were made with bismuth citrate (430 mg)+carbomer (1800 mg)+$H_2O$ (150 ml)+NaOH pellets (900 mg). This was stirred vigorously and left overnight to go translucent. These gels were precipitated with methanol (250 ml). The white precipitate was pelleted and dried. The dried precipitate was powdered before despatch. The Bi content was 8.74 wt %.

EXAMPLE 5

Patients and Methods

Thirty patients with radiological or endoscopic evidence of proctitis or procto-sigmoiditis with mildly or moderately active disease were included in the study.

Enemas (100 ml) prepared according to Example 2, were given to patients and were administered each night for four to eight weeks. Clinical and sigmoidoscopic evidence of improvement was observed in most of them.

In addition, in a controlled clinical trial these enemas were compared with enemas of mesalazine (2 g in 100 ml) given to similar patients for 4 weeks. Sigmoidoscopy and rectal biopsy were performed initially and after four weeks of treatment; patients kept a diary card and recorded daily symptoms of abdominal pain, general well being and the number and consistency of bowel motions; the presence of blood and mucus was also noted. Clinical and sigmoidoscopy findings were graded and blind histological grading of all biopsies was performed.

Results with the enema of Example 2 appeared to be at least as good as those given by the mesalazine treatment which is currently among the best treatments for proctitis.

EXAMPLE 6

Patients and Methods

Eleven patients having radiological or endoscopic evidence of proctitis or procto-sigmoiditis with mildly or moderately active disease were included in the study. The eleven patients had been in clinical relapse for between 1 week and 3 years (median 3 months) with 9 of the 11 in relapse for more than 2 months. Eight of the 11 patients were taking mesalazine at the time of relapse and continued to take this drug; none were receiving oral prednisolone or other rectal medication.

Enemas were prepared from De Nol which contains tripotassium dicitrato bismuthate and has a pH of 9.8. Patients were given 300 ml of this and a second bottle which contained a 1.2% Keltrol suspension (a thixotropic xanthan gum) with a phosphate buffer at pH4.6 and hydroxybenzoates as preservative. Patients used a graduated measure into which was poured 20 ml of De Nol and 20 ml of Keltrol—the 40 ml mixture containing 480 mg of Bismuth with a pH of 7.2 was used as the enema; these were administered each night for four weeks. Sigmoidoscopy and rectal biopsy were preformed initially and after four weeks of treatment; patients kept a diary card and recorded daily symptoms of abdominal pain, general well being and the number and consistency of bowel motions; the presence of blood and mucus was also noted. Clinical and sigmoidoscopy findings were graded and blind histological grading of all biopsies was performed.

Results

Of the 11 patients (5 men) there was symptomatic improvement in 5, whilst 6 remained unchanged. Sigmoidoscopic appearances were improved in 9, with no change in 2 and histological grading improved in 6, remained the same in 2 and was worse in 3. Topical treatment of proctitis and procto-sigmoiditis with bismuth enemas for four weeks improved overall scores of symptoms, sigmoidoscopic and histological appearances in 9 of 11 patients studied.

EXAMPLE 7

Granules of size in the range 0.5–2.1 mm were prepared by dry compacting and subsequently sieving a tablet mass containing a complex of bismuth citrate with carbopol 934P. The granules were then spray coated with an aqueous suspension containing EUDRAGIT L (Röhm Pharma GmbH, Darmstadt, Germany) in the ratio of 3:7 to provide a batch coated with 25% dry lacquer substance. The resulting granules had the following formulation:

| Material | |
|---|---|
| Bi/carbomer complex | 55.8 g |
| Lactose | 10.7 g |
| Povidone (i.e. PVP) | 1.2 g |
| Explotab (Na Starch glycolate) | 2.5 g |
| Mg stearate | 0.9 g |
| Talc | 10.6 g |
| EUDRAGIT L | 18.1 g |
| Antifoam emulsion SE 2 | 0.1 g |
| Total | 100.0 g |

The batch of coated granules was packed into hard gelatin capsules (LOK-CAP, Eli Lilly) in an amount of 800 mg granules per capsule.

We claim:

1. A water soluble complex of bismuth with a polyacrylate.

2. A complex as claimed in claim 1 wherein the polyacrylate is a carbomer.

3. A complex as claimed in claim 1 or 2 wherein the bismuth and polyacrylate are in a weight ratio of 1:7 to 5:1.

4. A complex as claimed in claim 1, wherein the bismuth is derived from a bismuth salt of a weak inorganic acid, a bismuth salt of a carboxylic acid, or bismuth hydroxide.

5. A complex as claimed in claim 4, wherein the bismuth salt is selected from the group consisting of bismuth citrate, bismuth subsalicylate and bismuth subgallate.

6. A complex as claimed in claim 1, comprising carbopol 934P and bismuth derived from bismuth citrate.

7. A pharmaceutical composition comprising a complex as claimed in claim 1.

8. A pharmaceutical composition as claimed in claim 7, including a disintegrant.

9. A pharmaceutical composition as claimed in claim 7, in a delayed or sustained-release dosage form for oral administration to deliver bismuth post-gastrically.

10. A pharmaceutical composition as claimed in claim 9, in the form of microgranules coated with a methyl methacrylate/methacrylic acid copolymer to provide delayed release of the bismuth.

11. A pharmaceutical composition as claimed in claim 7, in a form for rectal administration.

12. A pharmaceutical composition as claimed in claim 7, further comprising one or more active ingredients.

13. A pharmaceutical composition as claimed in claim 12, further comprising one or more pharmacologically active compounds selected from antibiotics and anti-protozoal agents.

14. A pharmaceutical composition as claimed in claim 13, comprising tetracycline as said antibiotic and Metronidazole as said anti-protozoal agent.

15. A process for the preparation of a water-soluble complex of bismuth and a polyacrylate comprising reacting a bismuth-containing compound with a polyacrylate in a liquid phase.

16. A method of treating inflammatory bowel disease which comprises the step of administering a pharmaceutically effective amount of a water-soluble complex of bismuth with a polyacrylate either orally in a delayed or sustained-release dosage form, or rectally.

17. A method as claimed in claim 16, wherein the bismuth is derived from bismuth citrate, the polyacrylate is a carbomer and administration is orally in a delayed or sustained-release dosage form.

18. A method as claimed in claim 17, wherein the carbomer is carbopol 934P and the weight ratio is about 1:2.

19. A method as claimed in claim 18, wherein said water-soluble complex is microencapsulated.

20. A method of treating *Helicobacter pylori* infection of the alimentary canal which method comprises the step of administering a pharmaceutically effective amount of a bismuth/polyacrylate complex as defined in claim 1.

21. A method as claimed in claim 20, wherein said complex also comprises tetracycline and Metronidazole.

* * * * *